(12) United States Patent
Carlsson et al.

(10) Patent No.: US 11,202,719 B2
(45) Date of Patent: Dec. 21, 2021

(54) OSTOMY APPLIANCE CONFIGURED FOR LEAKAGE DETECTION

(71) Applicant: Hollister Incorporated, Libertyville, IL (US)

(72) Inventors: Jonas P. Carlsson, Chicago, IL (US);
Michael P. Nolan, Chicago, IL (US);
Christina Augustyn, Chicago, IL (US);
James Brandon Barker, Antioch, IL (US); Ryan S. Park, Northbrook, IL (US); Scott Janis, El Cerrito, CA (US);
Stephanie Henze, San Mateo, CA (US);
Christopher Michael Wlezien, Evanston, IL (US); Somasunder Vijay Sekaran, San Francisco, CA (US);
Germain Verbrackel, San Francisco, CA (US); Robert Lane, Larkspur, CA (US); Scott E. Liddle, Raleigh, NC (US); Stephanie Musinsky, Raleigh, NC (US); Kyle A. Matthews, Chapel Hill, NC (US)

(73) Assignee: Hollister Incorporated, Libertyville, IL (US)

( * ) Notice: Subject to any disclaimer, the term of this patent is extended or adjusted under 35 U.S.C. 154(b) by 0 days.

(21) Appl. No.: 17/265,430

(22) PCT Filed: Oct. 3, 2019

(86) PCT No.: PCT/US2019/054476
§ 371 (c)(1),
(2) Date: Feb. 2, 2021

(87) PCT Pub. No.: WO2020/076605
PCT Pub. Date: Apr. 16, 2020

(65) Prior Publication Data
US 2021/0244563 A1 Aug. 12, 2021

Related U.S. Application Data

(60) Provisional application No. 62/803,125, filed on Feb. 8, 2019, provisional application No. 62/743,173, filed on Oct. 9, 2018.

(51) Int. Cl.
*A61F 5/445* (2006.01)
*A61F 5/44* (2006.01)

(52) U.S. Cl.
CPC ............ *A61F 5/445* (2013.01); *A61F 5/4401* (2013.01)

(58) Field of Classification Search
CPC .. A61F 5/448; A61F 5/445; A61F 2005/4483; A61F 2005/4486; A61F 5/443
See application file for complete search history.

(56) References Cited

U.S. PATENT DOCUMENTS

| 5,494,038 A | 2/1996 | Wang et al. |
| 8,087,298 B1 | 1/2012 | Dasch |
| (Continued) | | |

FOREIGN PATENT DOCUMENTS

| EP | 0635719 A2 | 1/1995 |
| WO | 2008124717 A2 | 10/2008 |
| WO | 2018028756 A1 | 2/2018 |

OTHER PUBLICATIONS

International Preliminary Report on Patentability and Written Opinion issued by ISA/EPO in connection with PCT/US2019/054476 dated Apr. 8, 2021.

*Primary Examiner* — Susan S Su
(74) *Attorney, Agent, or Firm* — Levenfeld Pearlstein, LLC

(57) ABSTRACT

An ostomy appliance includes an ostomy hydrocolloid having a body-facing side, a pouch-facing side and a stoma opening, at least one fluid aperture formed in the body- (Continued)

facing side and at least one fluidic channel embedded in the ostomy hydrocolloid having a proximal portion disposed in fluid communication with the at least one fluid aperture. The ostomy appliance also includes at least one window formed in the pouch facing side, the at least one window aligned with a distal portion of the fluidic channel such that a portion of the fluidic channel is visible through the window. In another embodiment, an ostomy appliance includes a skin barrier material and an ultrasonic detection device for monitoring the skin barrier material.

14 Claims, 8 Drawing Sheets

(56) References Cited

U.S. PATENT DOCUMENTS

| | | |
|---|---|---|
| 8,409,158 B2 | 4/2013 | Edvardsen et al. |
| 2003/0204174 A1* | 10/2003 | Cisko, Jr. ................. A61F 5/445 604/338 |
| 2017/0112658 A1 | 4/2017 | Hosono |

* cited by examiner

OSTOMY APPLIANCE CONFIGURED FOR LEAKAGE DETECTION

This is a National Stage Application of International Patent Application No. PCT/US2019/054476, filed Oct. 3, 2019, which claims the benefit of and priority to U.S. Provisional Application No. 62/743,173 filed Oct. 9, 2018 and to U.S. Provisional Application No. 62/803,125 filed Feb. 8, 2019, the entirety of which are incorporated fully herein by reference.

BACKGROUND

The following description relates generally to an ostomy appliance configured for leakage detection.

An ostomy pouch includes opposing sidewalls defining an internal collection area. One of the sidewalls is provided with an inlet opening to receive a stoma, and means to secure the pouch to the user. Such means include, for example, an ostomy barrier, faceplate or skin barrier ring, which may be connected to or formed integrally with the sidewall having the inlet opening. The ostomy barrier (or faceplate or barrier ring) may include adhesive on a skin-facing side to seal against the user's skin in an area surrounding the stoma. Such a system is intended to prevent or limit leakage of bodily waste discharged from the stoma through the stoma/barrier/pouch environment.

However, the seal formed between the ostomy barrier and the user may weaken, for example, with time, movement, improper installation and/or application of an external force, and thus, become susceptible to leaking. Often times, the user is unaware of, or cannot easily assess, the extent of weakening in the seal. Thus, a user is typically not aware of a weakened seal, and consequently, the risk of leakage, until a fluid discharged from the stoma leaks through to an exterior of the seal (i.e., the barrier) and becomes undesirably exposed to an external environment outside of the stoma/barrier/pouch environment.

Efforts have been made in the art to detect leakage of fluid before the fluid escapes to the exterior environment. For example, U.S. Pat. No. 8,409,158 ("US '158") discloses an ostomy device having an adhesive wafer for attaching to the skin around a stoma. The wafer includes an adhesive layer having a proximal adhesive side and a distal side, where the distal side is covered with a backing layer. The wafer also includes a central portion and a peripheral portion and further includes a proximal section located on the proximal side of the central portion and a distal section visually arranged on the distal side of the peripheral portion. The distal section changes color when the proximal section is exposed to fluid.

However, leakage indicators described in the ostomy device of US '158 may require frequent inspection by the user or may be difficult to perceive.

Accordingly, it is desirable to provide an ostomy appliance, such as an ostomy hydrocolloid or ostomy pouch having such an ostomy hydrocolloid, in which leakage may be detected using a sensor. It is also desirable to provide an ostomy appliance in which a notification may be provided to the user based on leakage detection by the sensor, before the leakage reaches the exterior environment.

SUMMARY

In one aspect, an ostomy appliance may include an ostomy hydrocolloid having a body-facing side, a pouch-facing side and a stoma opening, at least one fluid aperture formed in the body-facing side, at least one fluidic channel embedded in the ostomy hydrocolloid having a proximal portion disposed in fluid communication with the at least one fluid aperture, and at least one window formed in the pouch facing side. The at least one window is aligned with the distal portion of the fluidic channel such that a portion of the fluidic channel is visible through the window.

The ostomy appliance may also include a color indicator disposed in the at least one fluidic channel between the proximal portion and the distal portion. The at least one fluidic channel may be made from a wicking material and may be configured to draw fluid from the at least one fluid aperture toward the distal portion. The at least one fluid aperture may include a plurality of fluid apertures disposed about the stoma opening. The fluid apertures of the plurality of fluid apertures may be disposed concentrically about the stoma opening. The at least one fluidic channel may include a plurality of fluidic channels and the at least one window may include a plurality of windows. The fluid apertures of the plurality of fluid apertures may be disposed in fluid communication with the fluidic channels of the plurality of fluidic channels, and the windows of the plurality of windows may be aligned with visible portions of the fluidic channels.

The ostomy hydrocolloid may include a skin barrier, a film and a backing layer. The ostomy hydrocolloid may also include a coupling section on the pouch-facing side.

According to one embodiment, the ostomy appliance may further include a sensor assembly configured for removable connection to the ostomy hydrocolloid. The sensor assembly may include at least one optical sensor configured to detect a color or a change in color at a visible portion of the at least one fluidic channel and output sensor information representative of the detected color or change in color.

The sensor assembly may further include a controller operably connected to the least one optical sensor. The controller may be configured to determine a leakage condition based on the sensor information. The at least one optical sensor may include a plurality of optical sensors, and the at least one window may include a plurality of windows. The optical sensors of the plurality of optical sensors may be substantially aligned with respective windows of the plurality of windows.

The sensor assembly may further include a substantially ring-shaped housing in which the plurality of optical sensors are disposed. The substantially ring-shaped housing may have a plurality of sensor windows configured for transmission of light to and from the plurality of optical sensors. The sensor assembly may further include a power supply operably connected to the controller and a releasable fastener configured to selectively fasten opposing ends of the housing to one another. The sensor assembly may further comprise a transceiver configured for wireless communication.

In one embodiment, the ostomy appliance may also include a notification device communicatively coupled to the sensor assembly via the transceiver. The notification device may be configured to output a notification based on the determined leakage condition.

In another aspect, an ostomy appliance may include a skin barrier material for attaching the ostomy appliance to a user's peristomal skin and an ultrasonic detection device configured to monitor the skin barrier material, an interface between the skin barrier material and the user's peristomal skin, and/or any material arranged between the skin barrier material and the user's peristomal skin. The ultrasonic detection device may include at least one ultrasonic transducer configured to transmit ultrasound waves through the skin barrier material and at least one receiver configured to detect the ultrasonic waves. The ultrasonic detection device may be configured to monitor at least one condition of the skin barrier material based on at least one characteristic of the ultrasonic waves traveling through the skin barrier material. In some embodiments, the at least one characteristic of ultrasonic wave may include a rate, amplitude, and/or phase of ultrasonic waves traveling through the skin barrier material. In such embodiments, the ultrasonic detection device may be configured to detect ostomy effluent leakage by detecting a change in the rate and/or the amplitude of ultrasonic waves traveling through the skin barrier material.

In an embodiment, the at least one ultrasonic transducer and the at least one receiver may be arranged at opposing peripheries of the ostomy appliance, such that the ultrasound waves generated by the at least one ultrasonic transducer are transmitted across the skin barrier material and detected by the at least one receiver. The at least one ultrasonic transducer and the at least one receiver may comprise a plurality of ultrasonic transducers and a plurality of receivers arranged spaced apart from each other and configured to monitor the skin barrier material at different locations.

In another embodiment, the ultrasonic detection device may include an ultrasonic transceiver configured to transmit and receive ultrasonic waves. The ultrasonic transceiver may be configured to transmit ultrasound waves through the skin barrier material and detect the ultrasound waves reflected and returning to the ultrasonic transceiver.

In an embodiment, the ostomy appliance may be a faceplate for a two-piece ostomy pouch system including a body-side coupling ring configured to engage with a pouch-side coupling ring provided on an ostomy pouch to attach the ostomy pouch to the faceplate. In another embodiment, the ostomy appliance may be an ostomy skin barrier for a one-piece ostomy pouch system attached to an ostomy pouch. In yet another embodiment, the ostomy appliance may be an ostomy skin barrier ring. In any of the foregoing embodiments, the skin barrier material may be a hydrocolloid. In some embodiment, the ostomy appliance may further include at least one wicking material arranged proximate the ultrasonic detection device to facilitate absorption of fluid by the skin barrier material. In an embodiment, the ultrasonic detection device may be provided as a separate stand-alone device, which may be arranged spaced apart from the ostomy appliance or in contact with the ostomy appliance and configured to monitor the ostomy appliance.

In another aspect, an ostomy appliance system may include an ultrasonic detection device and a wearable device removably connected to the ostomy appliance and operably connected to the ultrasonic detection device. The wearable device may include a housing, a power supply, and a controller operably connected to the power supply.

The controller may be configured to determine a condition of the ostomy appliance based on the at least one characteristic of the ultrasound waves detected by the ultrasonic detection device. For example, the controller may be configured to determine an ostomy effluent leakage condition based on a change in the at least one characteristic of the ultrasound waves traveling through the skin barrier material upon the skin barrier material being exposed to ostomy effluent. The wearable device may further include one or more output devices operably connected to the controller and configured to output a notification based on the determined condition. The wearable device also may include a wireless transceiver.

According to an embodiment, the ostomy appliance system may further include a personal communication device communicatively connected to the wearable device via the wireless transceiver. The personal communication device may be configured to output a notification based on a condition of the ostomy appliance. The personal communication device may be a smartphone.

Other objects, features, and advantages of the disclosure will be apparent from the following description, taken in conjunction with the accompanying sheets of drawings, wherein like numerals refer to like parts, elements, components, steps, and processes.

DETAILED DESCRIPTION

Figure 1:
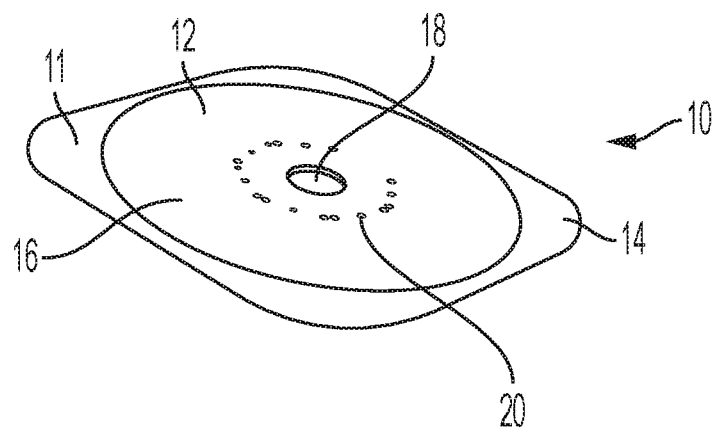
FIG. 1 is a perspective view of an ostomy appliance according to an embodiment.

While the present disclosure is susceptible of embodiment in various forms, there is shown in the drawings and will hereinafter be described one or more embodiments with the understanding that the present disclosure is to be considered illustrative only and is not intended to limit the disclosure to any specific embodiment described or illustrated.

FIG. 1 is a perspective view of an ostomy appliance 10 according to an embodiment. In one embodiment, the ostomy appliance 10 includes an ostomy hydrocolloid 11 configured to connect an ostomy pouch 310 (FIG. 11) to a user. The ostomy hydrocolloid 11 may be, for example, any of an ostomy barrier, an ostomy faceplate or an ostomy skin barrier ring. In one embodiment, the ostomy hydrocolloid 11 generally includes a skin barrier 12 and a backing layer 14.

The skin barrier 12 may include a known, medical grade adhesive suitable for adhering to the user's skin and sealing around a stoma. The backing layer 14 may be formed by a soft, flexible material that is generally soft and non-irritable to the user's skin, such as a nonwoven or foam material. The backing layer 14 may include an adhesive on a body-facing side 16 of the ostomy appliance 10, configured to adhere to the user in a peripheral region outside of the skin barrier 12.

The ostomy appliance 10 includes a stoma opening 18 extending through the skin barrier 12 and the backing layer 14. The stoma opening 18 is configured to receive the stoma and allow for flow of stoma fluid into the ostomy pouch.

At least one fluid aperture 20 is formed on the body-facing side 16 of the ostomy appliance 10, for example, in the skin barrier 12. In one embodiment, the at least one fluid aperture 20 includes a plurality of fluid apertures 20 discretely disposed about and spaced from the stoma opening 18. It is envisioned that the plurality of fluid apertures 20 may be disposed concentrically about the opening 18, but the present disclosure is not limited to such a configuration. For example, the fluid apertures 20 may be radially staggered relative to the stoma opening 18.

Figure 2:
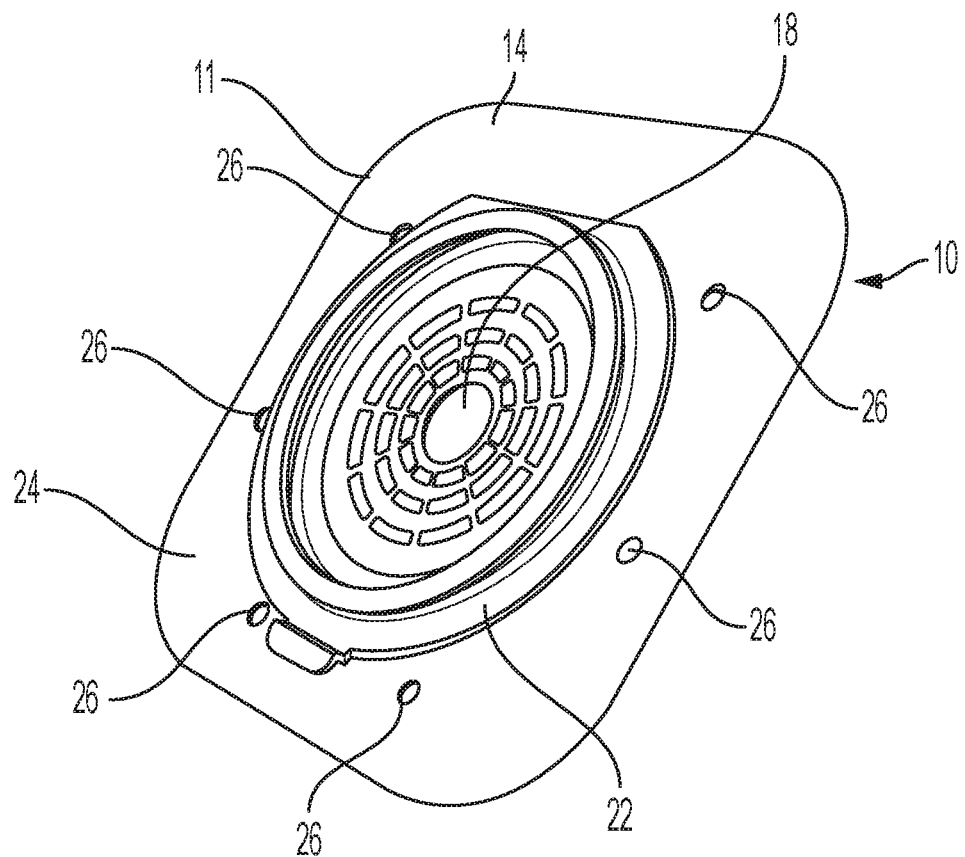
FIG. 2 is another perspective view of the ostomy appliance of FIG. 1.

FIG. 2 is another perspective view of the ostomy appliance 10 according to an embodiment. In one embodiment, the ostomy appliance 10 further includes a coupling section 22 at a pouch-facing side 24. In one embodiment, the coupling section 22 may be a known ostomy appliance flange configured for coupling to an ostomy pouch in a two-piece pouch configuration. In another embodiment, the coupling section 22 may be a known bag-barrier interface in a one-piece pouch configuration.

The ostomy appliance 10 further includes at least one window 26 at the pouch-facing side 24, extending through the backing layer 14. In one embodiment, the at least one window 26 includes a plurality of windows 26 spaced from the stoma opening 18. In one embodiment, the windows 26 are concentrically positioned about the stoma opening 18. However, the present disclosure is not limited to such an example. For instance, the windows 26 may be radially staggered relative to the stoma opening 18.

Figure 3:
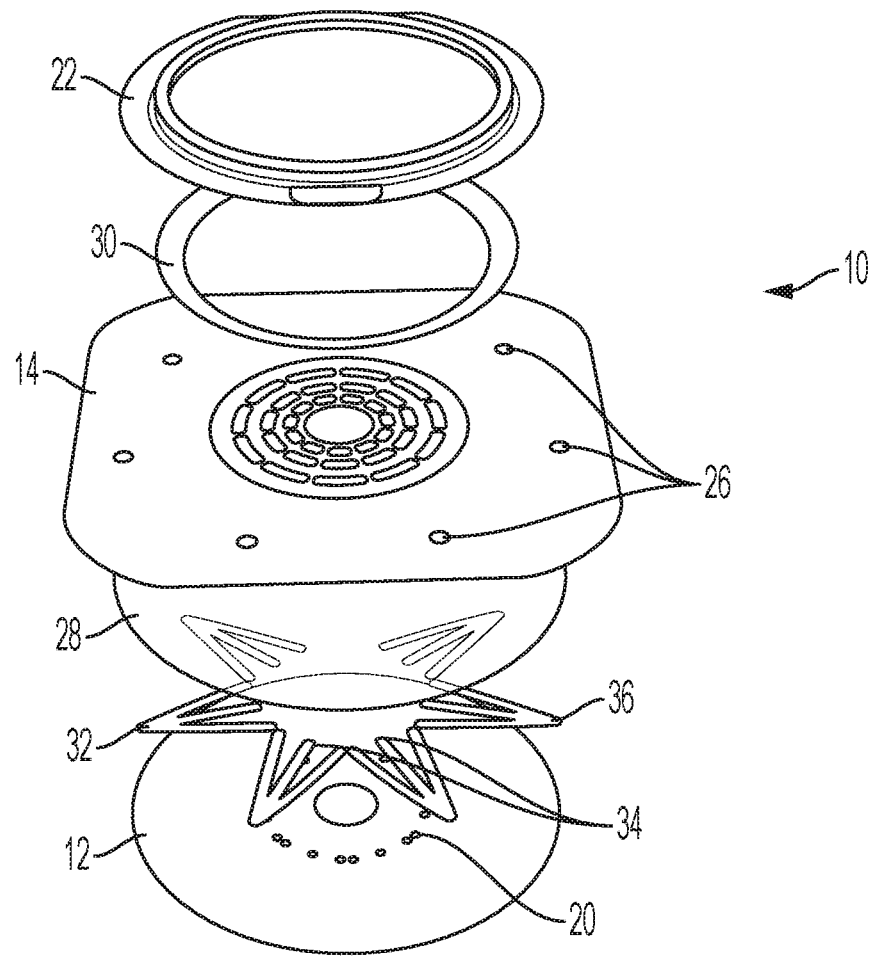
FIG. 3 is an exploded view of the ostomy appliance of FIG. 1.

FIG. 3 is an exploded view of the ostomy appliance 10 according to an embodiment. In one embodiment, an embedded film 28 is disposed between the skin barrier 12 and the backing layer 14. The embedded film 28 may be a laminate film and is preferably liquid impermeable. The embedded film 28 may be gas impermeable as well. The stoma opening 18 extends through the embedded film 28. Further, in one embodiment, the coupling section 22 may optionally be secured to the backing layer 14, directly or indirectly, with a flange attachment film 30.

At least one fluidic channel 32 is embedded in ostomy appliance 10. For example, in one embodiment, the at least one fluidic channel 32 may be disposed between the skin barrier 12 and the embedded film 28. The fluidic channel 32 includes a proximal portion 34 disposed in fluid communication with the at least one fluid aperture 20 and a distal portion 36 spaced from the proximal portion 34. In one embodiment, the distal portion 36 is disposed at a radial distance farther from the stoma opening 18 than the proximal portion 34. In one embodiment, the fluidic channel 32 may include a plurality of proximal portions 34 and a common distal portion 36 fluidically connected to the plurality of proximal portions 34. The proximal portion 34 and the distal portion 36 may be a proximal end and a distal end, respectively. In one embodiment, the at least one fluidic channel 32 includes a plurality of fluidic channels 32.

The fluidic channel 32 is formed of a material capable of transferring fluid from the proximal portion 34 to the distal portion 36. For example, the fluidic channel 32 may be formed of a wicking material through which a fluid may be transferred by capillary action.

Figure 4:
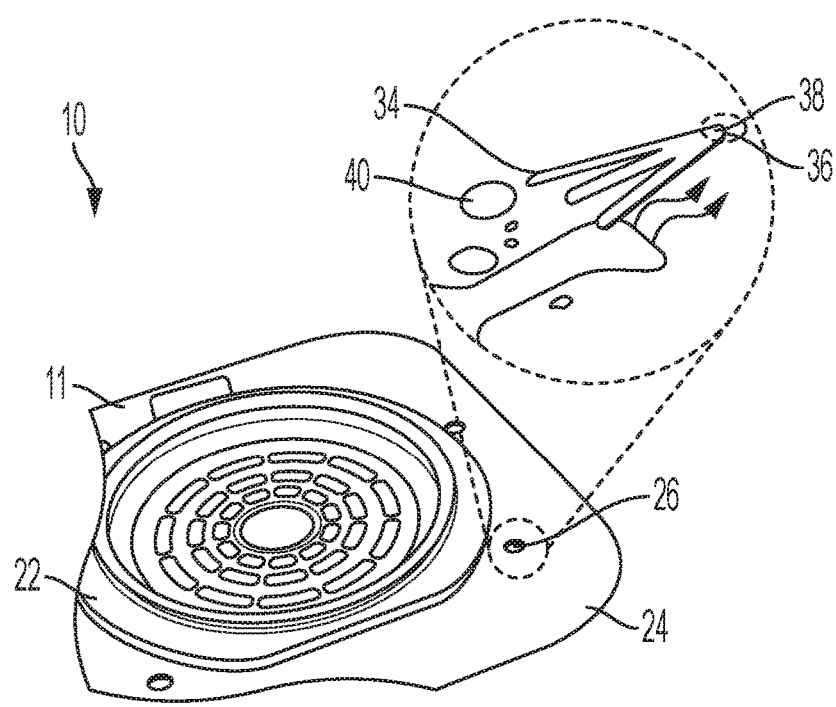
FIG. 4 is a perspective view of the ostomy appliance of FIG. 1 showing an enlarged cutaway section.

FIG. 4 is a perspective view of the ostomy appliance 10 showing an enlarged cutaway section view showing the fluidic channel 32 positioned relative to the window 26, according to an embodiment. In one embodiment, the window 26 is aligned with a visible portion 38 of the fluidic channel 32. The embedded film 28 is transparent or translucent or includes sections of transparent or translucent material aligned with the window 26. Accordingly, the visible portion 38 of the fluidic channel 32 is visible through the window 26 and the embedded film 28. In one embodiment, the visible portion 38 of the fluidic channel 32 is the distal portion 36 of the fluidic channel 32. In one embodiment, windows 26 of a plurality of windows 26 are aligned with respective visible portions 38 of a plurality of fluidic channels 32.

The at least one fluidic channel 32 may optionally include an embedded color indicator 40 between the proximal portion 34 and the visible portion 38. The color indicator 40 may be a biocompatible dye or other chemical configured to move through the fluidic channel 32 with a fluid.

Accordingly, in the embodiments above, stoma fluid may be received in the fluid aperture 20 and migrate into the fluidic channel 32, in the event of stoma fluid leakage from the stoma opening 18 between the ostomy appliance 11 and the user's skin. The fluid may move through the fluidic channel 32 from the proximal portion 34 toward the distal portion 36 and may be visible through the window 26 upon reaching the visible portion 38. In one embodiment, the color indicator 40 may also be visible at the visible portion 38 when the fluid reaches the visible portion 38.

Figures 5, 6:
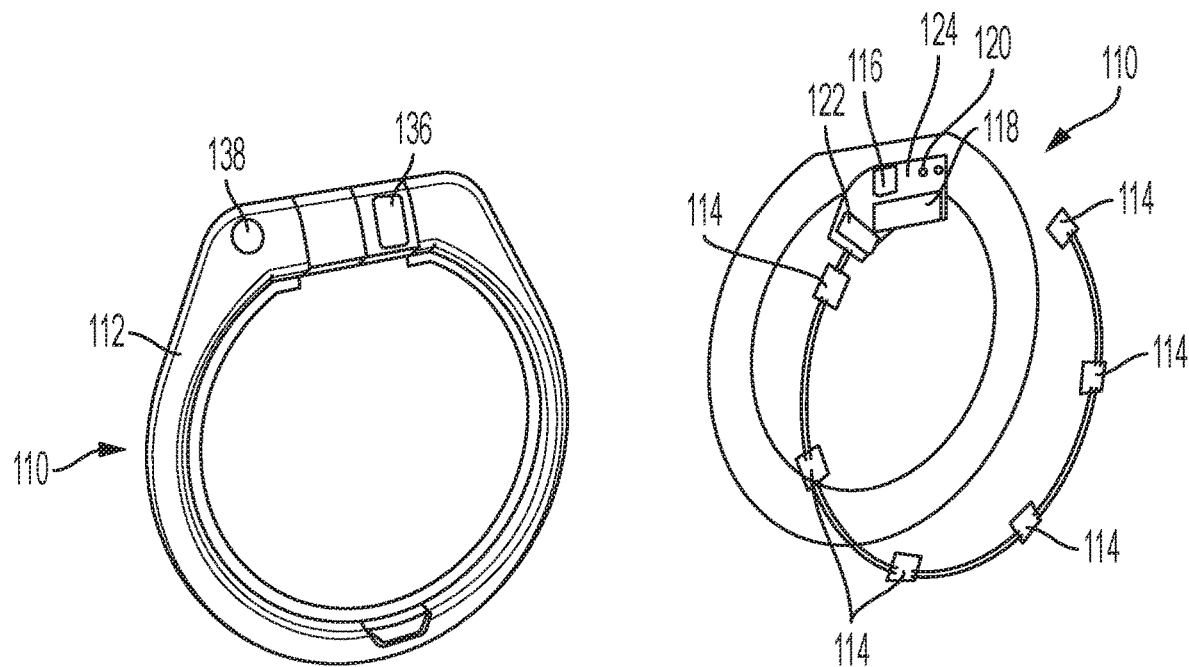
FIG. 5 is a perspective view of a sensor assembly of the ostomy appliance according to an embodiment.
FIG. 6 is a partially exploded view of the sensor assembly of FIG. 5, according to an embodiment.

FIG. 5 is a perspective view of a sensor assembly 110 of the ostomy appliance 10 according to an embodiment, and FIG. 6 is a partial exploded view of the sensor assembly 110 according to an embodiment. The sensor assembly 110 is configured to detect a color or a change in color of the visible portion 38. Accordingly, the sensor assembly 110 may detect that a fluid has reached the visible portion 38 of the fluidic channel 32 based on a change in color at the visible portion 38 caused by the fluid.

In one embodiment, the sensor assembly 110 includes a housing 112. The housing 112 may be made from a flexible, durable material, such as, but not limited to, silicone, polyurethane or materials having similar properties.

Referring to FIG. 6, the sensor assembly 110 further includes at least one sensor 114 operably connected to a controller 116. In one embodiment, a plurality of sensors 114 are operably connected to the controller 116. The sensor(s) 114 and the controller 116 may be interconnected by electrical circuitry, which may be flexible so to move with the housing 112.

The sensor 114 is an optical sensor configured to detect a color or change in color. Such optical sensors include, for example, a light sensor, reflective IR sensors, RGB sensors and other sensors capable of detecting a mild (white to off-white) or stark (white to black) color or color change.

The controller 116 may be a microcontroller and may include a processor, memory and communication module. The processor is configured to execute program instructions stored in the memory and the communication module is configured to send or receive signals to and from the processor to carry out operations based on the program instructions.

The sensor assembly 110 may further include a power supply 118, such as a battery, charging pads 120 for charging the power supply 118, and a transceiver 122 configured for electrical communications with one or more external devices as will be discussed further below. The controller 116, power supply 118, charging pads 120 and transceiver 122 may be operably connected to one another, for example, on a printed circuit board (PCB) 124.

In one embodiment, the transceiver 122 may be a wireless transceiver configured for wireless communications according to known wireless communication standards and protocols, and may communicate over known communication networks, such as personal area networks, wireless local area networks, metropolitan area networks and wide area networks. Accordingly, the transceiver 122 may be configured for various wireless communications including, but not limited to, Bluetooth, Bluetooth Low Energy, Near-Field Communication, WiFi, WiMax, cellular LTE or other cellular radio communications.

Figure 7:
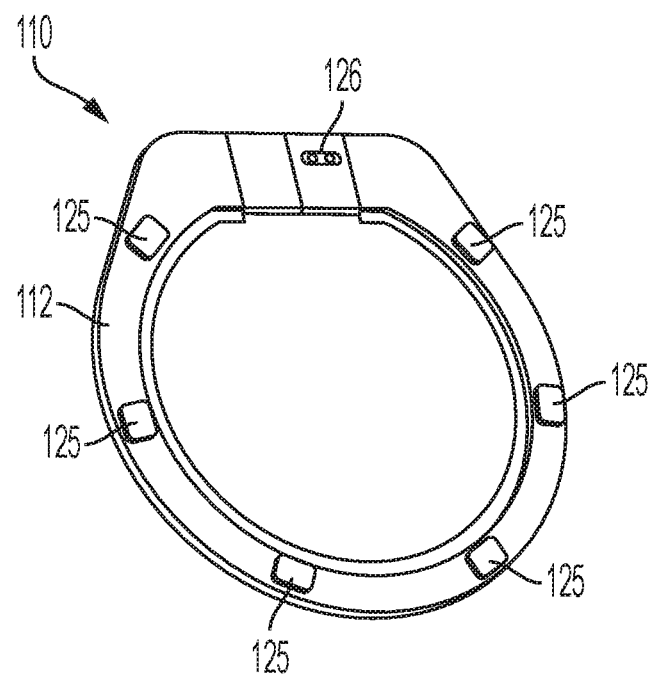
FIG. 7 is another perspective view of the sensor assembly of FIG. 5.

FIG. 7 is another perspective view of the sensor assembly 110, according to an embodiment. In one embodiment, the housing 112 may include one or more sensor windows 125 through which light may be transmitted to or from the at least one sensor 114. The housing 112 may also include a first charging interface 126 operably connected to the charging pads 120 (FIG. 6).

Figure 8:
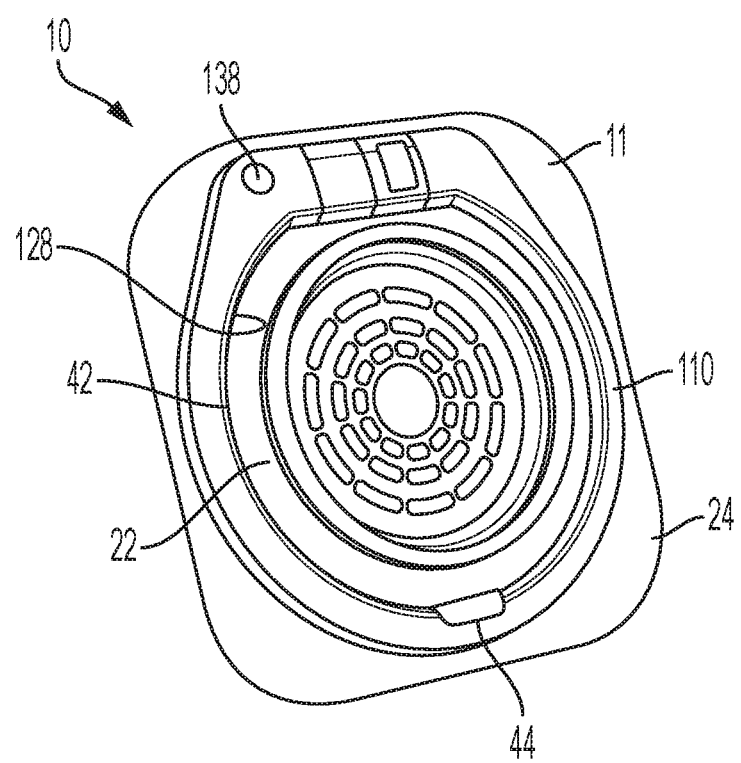
FIG. 8 is a perspective view of the ostomy appliance the a sensor assembly attached to an ostomy hydrocolloid, according to an embodiment.

FIG. 8 is a perspective view of the ostomy appliance 10, according to an embodiment. In one embodiment, the sensor assembly 110 is configured to be attached to the ostomy hydrocolloid 11, for example, at the pouch-facing side 24. For example, the sensor assembly 110 may fit around the coupling section 22. In one embodiment, an inner profile 128 of the housing 112 may be keyed to an outer profile 42 of the coupling section 22 for positioning of the sensor assembly 110 relative to the ostomy hydrocolloid 11 in a desired manner. In one embodiment, the coupling section 22 may also include a retaining tab 44 for holding the sensor assembly 110. In normal use, the sensor assembly 110 may be retained between the ostomy hydrocolloid 11 and the ostomy pouch 310.

Figure 9:
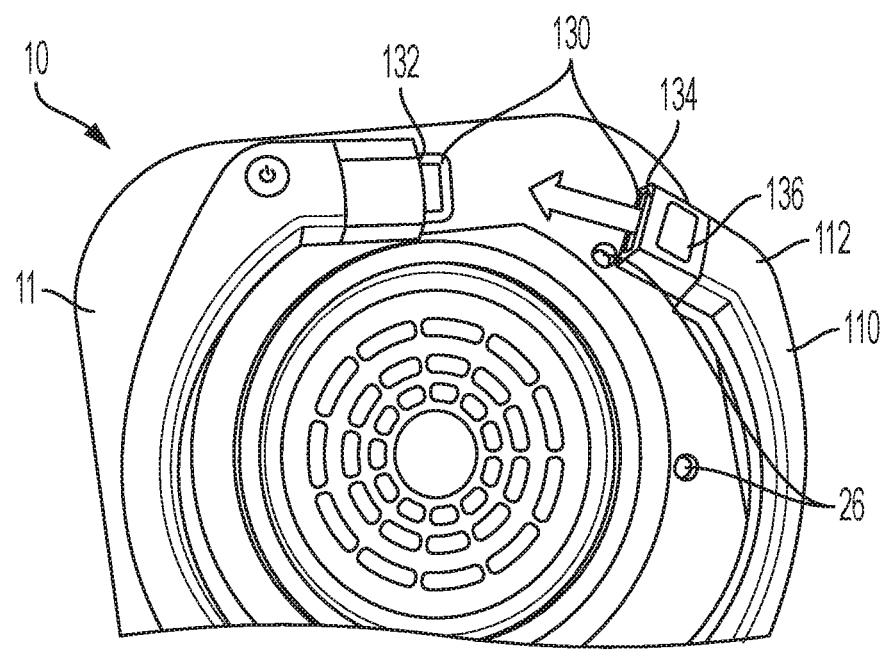
FIG. 9 is an enlarged view of a portion of the ostomy appliance of FIG. 9 with the sensor assembly in an open-ring condition.

FIG. 9 is an enlarged perspective view of the ostomy appliance 10 with the sensor assembly 110 in an open-ring configuration, according to an embodiment. The sensor assembly 110 is movable between a closed-ring configuration (FIG. 8) and the open-ring configuration of FIG. 9 through operation of a fastener 130. The fastener 130 may be, for example, a latch, a clasp, an adhesive, a clip or other suitable physical fastener. In the closed-loop configuration, the fastener 130 may be fastened to secure opposing ends 132, 134 of the housing 112 together. The fastener 130 may be released to move the sensor assembly 110 to the open-ring condition, where the opposing ends 132, 134 may be moved apart from another, for example, by flexing the housing 112. In one embodiment, the fastener 130 may be released by way of a pushbutton 136 or the like formed on the housing 112.

Referring now to FIGS. 2, 4 and 6-9, the sensor assembly 110 is configured to be positioned relative to the ostomy hydrocolloid 11 such that the at least one sensor 114 is substantially aligned with a corresponding window 26 of the ostomy hydrocolloid 11. Accordingly, the at least one sensor 114 is configured to detect a color or change in color of the visible portion 38 of the fluidic channel 32 through the window 26 of the ostomy hydrocolloid 11. In one embodiment, a plurality of sensors 114 are aligned with a plurality of corresponding windows 26 of the ostomy hydrocolloid 11 such that a color or change in color at the visible portion 38 may be detected at a plurality of locations.

Figures 10A, 10B, 10C:
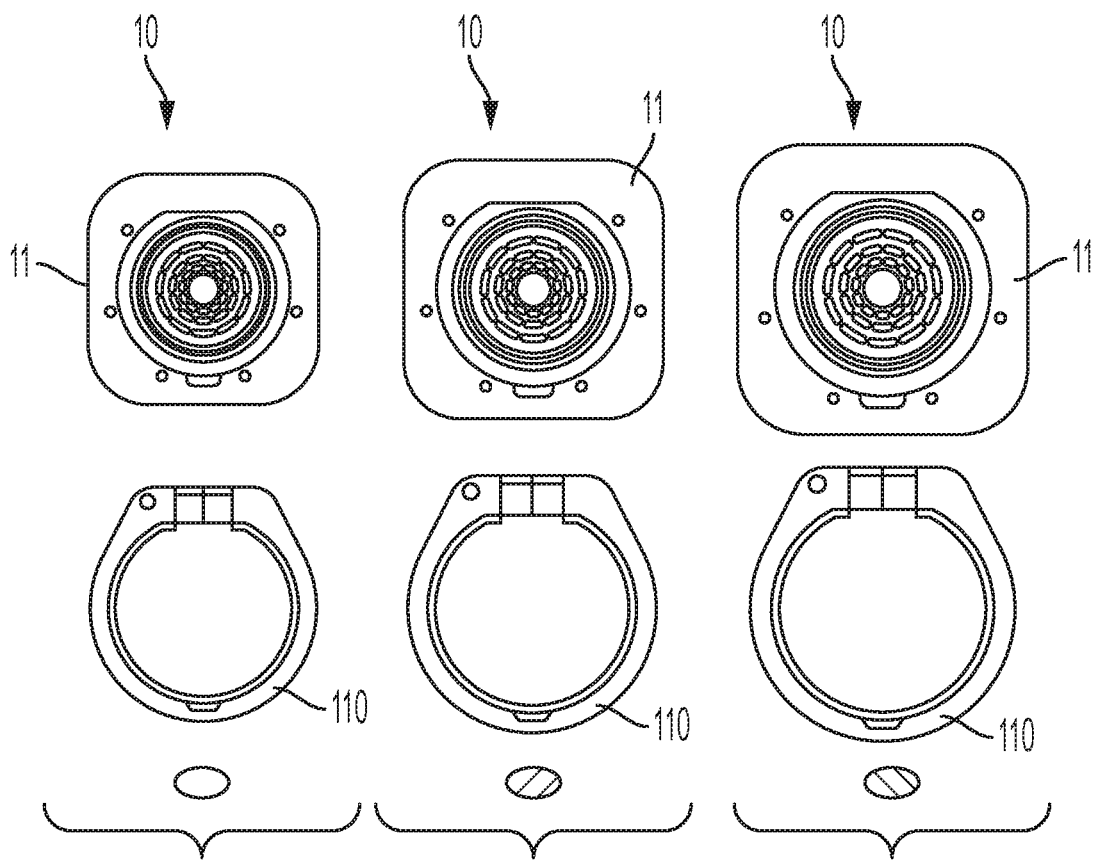
FIGS. 10A-C shows differently sized embodiments of the ostomy appliance according to embodiments.

FIGS. 10A-10C show the ostomy appliance 10 with the sensor assembly 110 disconnected from the ostomy hydrocolloid 11 according to an embodiment. As shown in FIGS. 10A-10C, it is envisioned that the ostomy appliance 10 may be formed in different sizes by manufacturing the ostomy hydrocolloid 11 and the sensor assembly 110 as differently sized pairs for use with one another.

Figure 11:
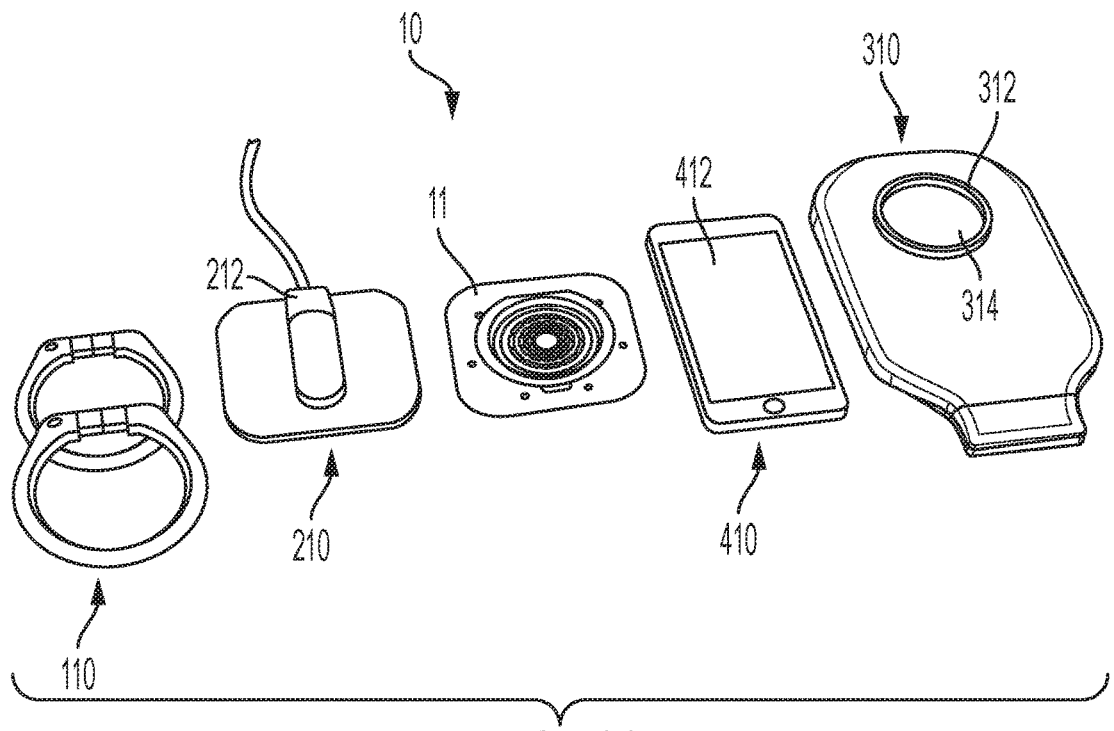
FIG. 11 shows various components of the ostomy appliance according to embodiments.

FIG. 11 shows additional components which may be part of, or configured for use with, the ostomy appliance 10, according to an embodiment. In one embodiment, a charging device 210 may include a second charging interface 212 configured for operable connection with the first charging interface 126 of the sensor assembly 110 to charge the power supply 118.

The ostomy appliance 10 may further include an ostomy pouch 310 configured for coupling with the ostomy hydrocolloid 11. In one embodiment, the ostomy pouch 310 may be coupled to the ostomy hydrocolloid 11 at the coupling section 22 by way of a corresponding pouch coupling section 312. An inlet opening 314 is included in the ostomy pouch 310 and is configured for alignment with the stoma opening 18. In another embodiment, the ostomy pouch 310 and the ostomy hydrocolloid 11 are formed as a one-piece construction.

A notification device 410 may be communicatively connected to the to the sensor assembly 110. In one embodiment, the notification device 410 may be may be a mobile communication device such as a smartphone or other mobile phone communicatively connected to the sensor assembly 110 via the transceiver 122 over a wireless communication interface. Alternatively, or in addition, the notification device 410 may be another mobile communication device, portable electronic device, or other electronic device configured for communication, directly or indirectly, with the sensor assembly 110. Such devices may include, but are not limited to, tablets, laptop computers, desktop computers, smart speakers, connected wearable accessories such as fitness trackers, smart watches and the like, smart televisions, personal digital assistants and the like. In some embodiments, the notification device 410 may be operably connected to sensor assembly 110 over either a wired connection or wireless connection. In one embodiment, the notification device 410 includes a display screen 412.

In one embodiment, the notification device 410 may be integrated with the sensor assembly 110. For example, the notification device 410 may be disposed within the housing 112 and operably connected to the controller 116.

In one embodiment, the sensor assembly 110 may be paired, synced, or otherwise communicatively connected to the notification device 410, with a known operation, which may be initiated, for example, by operation of a power and/or sync button 138 (FIGS. 5 and 8) on the sensor assembly 110.

In one embodiment, the at least one sensor 114 may provide sensor information to the controller 116. The sensor information may include, for example, a detected color of the visible portion 38, a detected change in color of the visible portion 38, or both. In one embodiment, the sensor information may be provided as raw analog or digital data. In one embodiment, the sensor information may also include identification information of the sensor 114. With a position of the sensor 114 known, a location of the detected color or change in color may be determined.

A leakage condition of the ostomy appliance 10 may be determined based on the sensor information. In one embodiment, the determined leakage condition may indicate that stoma fluid leakage is not detected, that stoma fluid leakage is detected, and in one embodiment, an extent of the detected stoma fluid leakage.

In one embodiment, a condition indicating that stoma fluid leakage is not detected may be determined when the detected color of the visible portion 38 corresponds to a known color associated with a "dry" (i.e., no stoma fluid present) visible portion, or conversely, if the detected color of the visible portion does not correspond to a known color associated with a "wet" (i.e., stoma fluid present) visible portion. Alternatively, or in addition, the condition indicating that stoma fluid leakage is not detected may be determined if the sensor 114 does not detect a change in color of visible portion 38, or detects a change in color that remains within a known range of colors associated with a "dry" visible portion 38.

In one embodiment, a condition indicating that stoma fluid leakage is detected may be determined if the detected color of the visible portion 38 corresponds to a known color associated with a "wet" visible portion 38, or conversely, if the detected color of the visible portion 38 does not correspond to a known color associated with a "dry" visible portion 38. Alternatively, or in addition, the condition indicating that stoma fluid leakage is detected may be determined if the sensor 114 detects a change in color of the visible portion 38, or detects a change in color that falls within a known range of colors associated with a "wet" visible portion 38.

In one embodiment, the extent of detected stoma fluid leakage may refer to how widespread the detected stoma fluid leakage is across the ostomy hydrocolloid 11. For example, the extent of stoma fluid leakage may be determined based on the number of sensors 114 which have detected the stoma fluid leakage at respective visible portions 38. In one embodiment, the extent of detected stoma fluid leakage may also refer to a distance from a reference point, such as the stoma opening 18 or outer periphery of the ostomy hydrocolloid, that the stoma fluid leakage has migrated. Such an extent may be determined, for example, by staggering the fluid apertures 20 radially relative to the stoma opening 18. The locations of visible portions 38 of fluidic channels 32 which correspond to different fluid apertures 20 may be known. Accordingly, in one embodiment, an extent of stoma fluid leakage may be determined based on the known relationship between the position of a fluid aperture 20 relative to the stoma opening 18 and the visible portion 38 of the fluidic channel 32 fluidically connected to the fluid aperture 20.

The condition may be determined, for example, at the sensor assembly 110, the notification device 410, or both. For example, the controller 116 of the sensor assembly 110 may determine the condition based on the sensor information. The sensor assembly 110 may transmit the determined condition to the notification device 410, for example, over a wireless communication interface with the transceiver 122. Alternatively, or in addition, the sensor assembly 110 may transmit the sensor information to the notification device 410 and the notification device 410 may be configured to determine the condition in the manner described above.

In one embodiment, the notification device 410 may periodically receive the determined condition from the sensor assembly 110. Alternatively, or in addition, a user may operate the notification device 410 to request the determined condition from the sensor assembly 110 and, in response to receiving the request, the sensor assembly 110 may determine and transmit the condition to the notification device 410.

In one embodiment, the notification device 410 is configured to output a notification based on the determined condition. The notification may be one or more of an audio notification, a visual notification or a vibratory notification to be sensed by the user. In one embodiment, the notification may include graphics, text, symbols, representative models of the ostomy hydrocolloid 11 and the like, which may be provided on a display 412 of the notification device 410. In one embodiment, the notification may vary depending on the determined condition. For example, the notification may vary in type, frequency, intensity, volume, brightness, pattern, or the like. In one embodiment, the notification may include instructions to replace the ostomy hydrocolloid 11.

In one embodiment, the notification device 410, embodied as a smartphone, may perform functions according to a smartphone application directed to the ostomy appliance 10. The smartphone application may include program instructions stored in a memory unit of the smartphone which are configured to be executed by a processor of the smartphone to control the smartphone to perform the functions. For example, the smartphone may be controlled to generate and output the notification. The smartphone may also be controlled to store additional data and enable further communications. For example, the smartphone may be configured to track leaks or degradation of the ostomy hydrocolloid 11, behaviors and activities that could potentially affect wear time, including, but not limited to: pouch changes, diet, leakage occurrence, gas occurrence and physical activity.

In one embodiment, the smartphone may be configured to provide a platform to share practices and advice from other users and clinicians. In one embodiment, the smartphone may be configured to allow for communication with other information sources, for example, to access video tutorials providing additional education and instruction on managing a stoma. In one embodiment, the smartphone may be configured to allow for pictures to be taken and stored of the stoma and skin health. In one embodiment the smartphone may be configured to facilitate contact with a wound, ostomy and continence (WOC) nurse (also referred to as an enterostomal therapy (ET) nurse), for example, to troubleshoot or share stoma and skin health conditions. In one embodiment, the smartphone may be configured to allow for ordering or automatic re-ordering of an ostomy appliance 10 or related supplies when a determination is made that such supplies are running low. In one embodiment, the smartphone may be configured to provide usage and patient data to, for example, the ostomy appliance manufacturer, such as marketing, research and product support teams. In one embodiment, such usage and data may be provided, for example, after a user opts-in, and the data may be provided securely, anonymously, and/or in accordance with local privacy laws and regulations, to support health economics.

Those having ordinary skill in the art will appreciate that the present disclosure is not limited to a smartphone application executed to control functions of a smartphone according to the examples above. For instance, it is also envisioned that a similar software application could be executed by a tablet or other portable device, a remote server configured to be accessed by the user through a known communications interface, or at a personal computing device, such as a laptop or desktop computer, or some combination of the above.

Figures 12A, 12B, 12C:
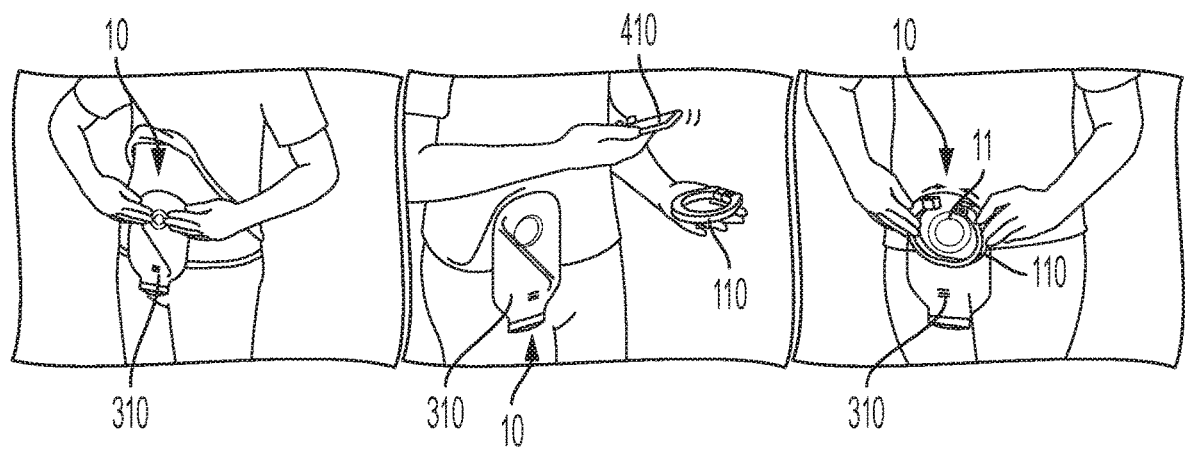
FIGS. 12A-12C show examples of a user configuring the ostomy appliance for use, according to an embodiment.

FIGS. 12A-12C show examples of a user configuring the ostomy appliance 10 for use, according to an embodiment. For example, the user may secure ostomy pouch 310 (FIG.

12A), communicatively connect the notification device 410 to the sensor assembly 110 (FIG. 12B) and connect the sensor assembly 110 to the ostomy hydrocolloid 11 (FIG. 12C).

Figures 13A, 13B, 13C:
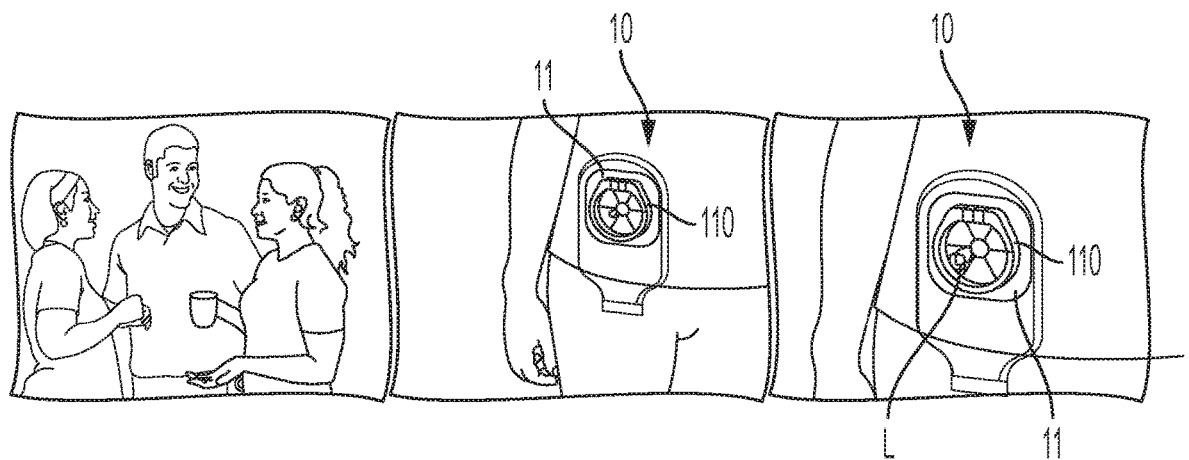
FIGS. 13A-13C show examples of a user during normal use of the ostomy appliance, according to an embodiment.

FIGS. 13A-13C show examples of a user during normal use of the ostomy appliance 10, according to an embodiment. For example, the user may interact in a social setting (FIG. 13A), the sensor assembly 110 may monitor the ostomy appliance 10 for stoma fluid leakage (FIG. 13B), and the sensor assembly 110 may detect stoma fluid leakage 'L' along the ostomy hydrocolloid 11 (FIG. 13C).

Figures 14A, 14B, 14C:
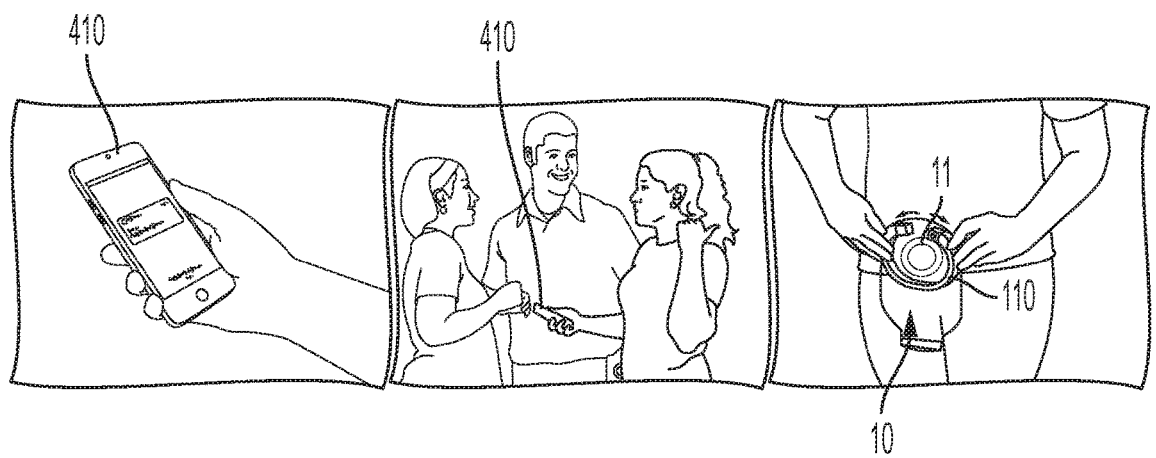
FIGS. 14A-14C show examples of a user receiving a notification of an ostomy appliance condition and tending to the ostomy appliance, according to an embodiment.

FIGS. 14A-14C show examples of a user receiving a notification of a leakage condition and tending to the ostomy appliance 10, according to an embodiment. For example, a notification of the leakage condition may be output on the notification device 410 (FIG. 14A), the user may move to a location to tend to the ostomy appliance 10 (FIG. 14B) and the user may remove the sensor assembly 110 from the ostomy hydrocolloid 11 (FIG. 14C) to replace the ostomy hydrocolloid 11.

Figure 15:
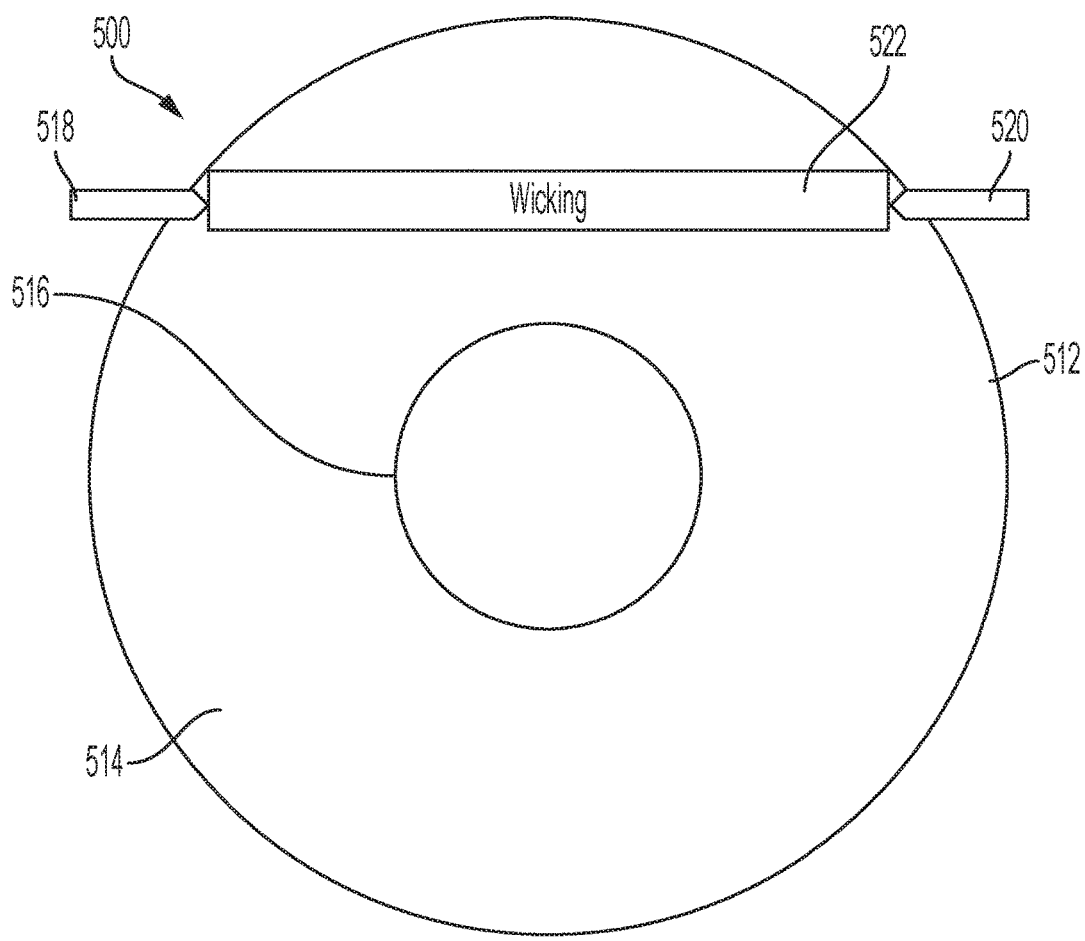
FIG. 15 is a schematic illustration of an ostomy appliance according to an embodiment.

FIG. 15 is a schematic illustration of an ostomy appliance 500 configured for ultrasonic fluid detection according to an embodiment. The ostomy appliance 500 may be configured as a faceplate assembly for a two-piece ostomy pouch system, an ostomy barrier for a one-piece ostomy pouch system, an ostomy skin barrier ring, and the like. The ostomy appliance 500 may include a skin barrier material 512 provided on a body-facing side 514 for adhering to user's skin. The skin barrier material 512 may be formed from a suitable medical grade adhesive, such as a hydrocolloid adhesive. A backing layer (not shown) may be provided on a pouch-facing side of the ostomy appliance 500. The backing layer may be formed from a soft, flexible material that is generally soft and non-irritable to the user's skin, such as a nonwoven or foam material. The ostomy appliance 500 may include a stoma opening 516 configured to receive the stoma and allow for passage of stoma fluid into an ostomy pouch (not shown.)

In an embodiment, the ostomy appliance 500 may be configured as a faceplate for a two-piece ostomy pouch system. In such an embodiment, the ostomy appliance 500 may include a body-side coupling ring (not shown) attached the pouch-facing side of the ostomy appliance 500. The body-side coupling ring may be configured to releasably engage a pouch-side coupling ring (not shown) provided on a pouch to attach the pouch to the ostomy appliance 500. In another embodiment, the ostomy appliance 500 may be configured as an ostomy barrier for a one-piece ostomy pouch system, wherein the pouch-facing side of the ostomy appliance 500 is sealed to a pouch wall proximate a stoma opening of the pouch.

The ostomy appliance 500 may include an ultrasonic fluid detection device. The ultrasonic fluid detection device may include at least one ultrasonic transducer and at least one receiver, which may be integrated into or arranged on or around the ostomy appliance 500. For example, the ultrasonic transducer and receiver may be embedded in the skin barrier material 512 or arranged at a periphery of the skin barrier material 512.

In the embodiment of FIG. 15, the ultrasonic fluid detection device may include an ultrasonic transducer 518 and a receiver 520. The ultrasonic transducer 518 and the receiver 520 may be arranged at opposing peripheries of the ostomy appliance 500. The ultrasonic transducer 518 and the receiver 520 may be arranged to contact the skin barrier material 512. The ultrasonic fluid detection device may be configured to measure and record a travel time of ultrasonic sound waves generated by the transducer 518 to reach the receiver 520 and/or amplitudes of the ultrasound waves. A rate of ultrasound waves traveling through the skin barrier material 512 may change when physical properties of the skin barrier material 512 is altered. For example, a rate of ultrasound waves traveling through the skin barrier material 512 may change when the skin barrier material 512 becomes wet by ostomy effluent. Further, an amplitude of ultrasound waves traveling through the skin barrier material 512 also may change because the skin barrier material 512 when wet may absorb or transmit the ultrasound waves differently when compared to the skin barrier material 512 prior to being exposed to fluid. As such, the ultrasonic fluid detection device may be configured to analyze the recorded travel times and amplitudes of the ultrasound waves to detect fluid leakage.

In some embodiments, the ultrasonic fluid detection device of the ostomy appliance 500 may comprise a plurality of ultrasonic transducers 518 and receivers 520 arranged spaced apart on or embedded in the ostomy appliance 500 in contact with the skin barrier material 512 to detect fluid leakage at multiple locations of the ostomy appliance 500.

In one embodiment, the ostomy barrier 500 may include at least one wicking material 522 arranged proximate the body-facing side 514 of the skin barrier material 512 to facilitate absorption of fluid. In the embodiment of FIG. 15, the wicking material 522 may be arranged between the ultrasonic transducer 518 and the receiver 520 to facilitate absorption of fluid by a portion of the skin barrier material 512 below the wicking material 522 to facilitate detection of fluid leakage.

In some embodiments, an ultrasonic transducer and a receiver may be arranged adjacent each other and configured to record reflected ultrasonic waves, similar to the known technology used for pregnancy sonograms. In such embodiments, a travel time and/or amplitude of the reflected ultrasonic waves may be recorded.

Figure 16:
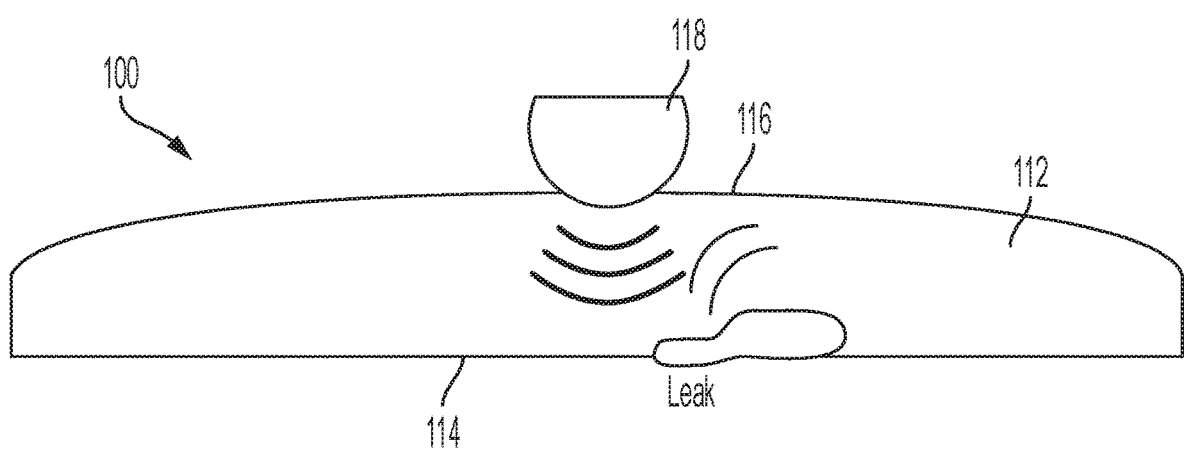
FIG. 16 is a schematic illustration of an ostomy appliance according to another embodiment.

FIG. 16 is a schematic illustration of an ostomy appliance 600 configured for ultrasonic leakage detection according to another embodiment. The ostomy appliance 600 may be configured similar to the ostomy appliance 500 generally comprising a skin barrier material 612 and an ultrasonic fluid detection device. In this embodiment, the ultrasonic fluid detection device may include an ultrasonic transceiver 618 configured to transmit and receive ultrasonic waves. The ultrasonic transceiver 618 may be embedded in or arranged on a pouch-facing side 616 of the ostomy appliance 600. The ultrasonic transceiver 618 may be configured to generate and transmit ultrasonic waves through a thickness of the skin barrier material 612 and record travel times and/or amplitudes of the ultrasonic waves reflected and returning to the transceiver 618. In such an embodiment, the ultrasonic transceiver 618 may be configured to record and analyze travel times and/or amplitudes of the reflected ultrasonic waves to detect ostomy effluent leakage at a body-facing side 614 of the ostomy appliance 600.

In some embodiments, the skin barrier material 512, 612 may comprise at least one material configured to amplify changes in characteristics of ultrasonic waves traveling through the skin barrier material 512, 612 in response to the skin barrier material 512, 612 being in contact with fluid or becoming wet, for example, cellulosic paper. For example, the skin barrier material 512, 612 may be formulated with at least one material configured to change a travel time or amplitude of ultrasound waves more drastically when wet.

In the embodiments above, the ostomy appliance 500, 600 may be monitored for one or more conditions on the basis of the characteristics of ultrasound waves traveling through skin barrier material 512, 612, such as traveling time and amplitudes, detected at the receiver 520, 618. Such conditions may include, but are not limited to, stoma fluid leakage and seal degradation.

The ostomy appliance 500, 600 may also include an electrically-attached controller configured to analyze the ultrasonic waves recorded by the receiver and alert a user of a potential leak via audio, vibrational, optical or tactile alerts. In some embodiments, the ostomy appliance 500, 600 may be provided with a wearable device including a controller, a power supply, such as a battery, and a wireless transceiver. The wearable device may be removably connected to the ostomy appliance 500, 600, for example, by way of friction fit, interference fit, clamping, mechanical interlock, or other suitable fastening mechanism.

The controller may be a microcontroller and may include a processor, memory, and communication module. The processor may be configured to execute program instructions stored in the memory, and the communication module may be configured to send or receive signals to and from the processor to carry out operations based on the program instructions. The wireless transceiver may be configured for wireless communications according to known wireless communication standards and protocols and may communicate over known communication networks, such as personal area networks, wireless local area networks, metropolitan area networks and wide area networks. Accordingly, the wireless transceiver may be configured for various wireless communications including, but not limited to, Bluetooth, Bluetooth Low Energy, Near-Field Communication, WiFi, WiMax, cellular LTE or other cellular radio communications. In one embodiment, the wireless transceiver may be a Bluetooth enabled microchip.

In one embodiment, the wearable device may include one or more output devices operably connected to the controller, such as a visual indicator, an audio indicator, or both. Alternatively, or in addition, other output devices may be envisioned as well, such as a vibrating indicator. The visual indicator may include, for example, a light emitting diode (LED) or a display, such as a liquid crystal display (LCD).

In one embodiment, the ostomy appliance 500, 600 may be communicatively coupled to a personal notification device. The personal notification device may be communicatively coupled to the wearable device over a wireless communication interface via the wireless transceiver. In one embodiment, the personal notification device may be a mobile communication device, such as a smartphone or other mobile phone. Alternatively, or in addition, the personal notification device may be another mobile communication device, a portable electronic device, or other electronic device configured for communication, directly or indirectly, with the wearable device. Such devices may include, but are not limited to, tablets, laptop computers, desktop computers, smart speakers, connected wearable accessories such as fitness trackers, smart watches and the like, smart televisions, personal digital assistants and the like.

In one embodiment, the wearable device may be paired, synced, or otherwise communicatively connected to the personal notification device with a known pairing or syncing operation, which may be initiated, for example, by operation of a switch.

All patents referred to herein, are hereby incorporated herein in their entirety, by reference, whether or not specifically indicated as such within the text of this disclosure.

In the present disclosure, the words "a" or "an" are to be taken to include both the singular and the plural. Conversely, any reference to plural items shall, where appropriate, include the singular. In additions, various features described with respect to any of the embodiments above may be used together, implemented in, or replace features in any of the other embodiments described above.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

The invention claimed is:

1. An ostomy appliance comprising:
   an ostomy hydrocolloid having a body-facing side, a pouch-facing side and a stoma opening;
   at least one fluid aperture formed in the body-facing side;
   at least one fluidic channel embedded in the ostomy hydrocolloid having a proximal portion disposed in fluid communication with the at least one fluid aperture;
   at least one window formed in the pouch facing side, the at least one window aligned with a distal portion of the fluidic channel such that a portion of the fluidic channel is visible through the window; and
   a sensor assembly configured for removable connection to the ostomy hydrocolloid, the sensor assembly comprising at least one optical sensor configured to detect a color or change in color at a visible portion of the at least one fluidic channel and output sensor information representative of the detected color or change in color.

2. The ostomy appliance of claim 1, further comprising a color indicator disposed in the at least one fluidic channel between the proximal portion and the distal portion.

3. The ostomy appliance of claim 1, wherein the at least one fluidic channel is made from a wicking material and is configured to draw fluid from the at least one fluid aperture toward the distal portion.

4. The ostomy appliance of claim 1, wherein the at least one fluid aperture comprises a plurality of fluid apertures disposed about the stoma opening.

5. The ostomy appliance of claim 4, wherein the fluid apertures of the plurality of fluid apertures are disposed concentrically about the stoma opening.

6. The ostomy appliance of claim 4, wherein the at least one fluidic channel includes a plurality of fluidic channels and the at least one window includes a plurality of windows, wherein the fluid apertures of the plurality of fluid apertures are disposed in fluid communication with the fluidic channels of the plurality of fluidic channels, and the windows of the plurality of windows are aligned with visible portions of the fluidic channels.

7. The ostomy appliance of claim 1, wherein the ostomy hydrocolloid comprises a skin barrier, a film and a backing layer.

8. The ostomy appliance of claim 1, further comprising a coupling section on the pouch-facing side.

9. The ostomy appliance of claim 1, wherein the sensor assembly further comprises a controller operably connected to the least one optical sensor, wherein the controller is configured to determine a leakage condition based on the sensor information.

10. The ostomy appliance of claim 9, wherein the at least one optical sensor includes a plurality of optical sensors, and the at least one window includes a plurality of windows, wherein the optical sensors of the plurality of optical sensors are substantially aligned with respective windows of the plurality of windows.

11. The ostomy appliance of claim 10, wherein the sensor assembly further comprises:
a substantially ring-shaped housing in which the plurality of optical sensors are disposed, the substantially ring-shaped housing having a plurality of sensor windows configured for transmission of light to and from the plurality of optical sensors.

12. The ostomy appliance of claim 11, wherein the sensor assembly further comprises a power supply operably connected to the controller, and a releasable fastener configured to selectively fasten opposing ends of the housing to one another.

13. The ostomy appliance of claim 12, wherein the sensor assembly further comprises a transceiver configured for wireless communication.

14. The ostomy appliance of claim 13, further comprising notification device communicatively coupled to the sensor assembly via the transceiver, the notification device configured to output a notification based on the determined leakage condition.

* * * * *